US011752491B2

(12) United States Patent
Hong et al.

(10) Patent No.: US 11,752,491 B2
(45) Date of Patent: Sep. 12, 2023

(54) CATALYST FOR CONVERSION OF CARBON DIOXIDE TO METHANOL BY HYDROGENATION, AND METHOD FOR PREPARING THE SAME

(71) Applicants: Hyundai Motor Company, Seoul (KR); Kia Motors Corporation, Seoul (KR); Research & Business Foundation Sungkyunkwan University, Gyeonggi-do (KR)

(72) Inventors: Chae Hwan Hong, Seoul (KR); Jin Woo Choung, Suwon Gyeonggi-do (KR); Jong Wook Bae, Gyeonggi-do (KR); Tae Yeol Goag, Gyeonggi-do (KR)

(73) Assignees: Hyundai Motor Company, Seoul (KR); Kia Motors Corporation, Seoul (KR); Research & Business Foundation Sungkyunkwan University, Suwon (KR)

( * ) Notice: Subject to any disclaimer, the term of this patent is extended or adjusted under 35 U.S.C. 154(b) by 253 days.

(21) Appl. No.: 17/035,144

(22) Filed: Sep. 28, 2020

(65) Prior Publication Data

US 2021/0402377 A1 Dec. 30, 2021

(30) Foreign Application Priority Data

Jun. 25, 2020 (KR) .......................... 10-2020-0077601

(51) Int. Cl.
*B01J 23/44* (2006.01)
*B01J 35/10* (2006.01)
*B01J 37/08* (2006.01)
*B01J 23/10* (2006.01)
*B01J 23/08* (2006.01)
(Continued)

(52) U.S. Cl.
CPC ............... *B01J 23/44* (2013.01); *B01J 23/08* (2013.01); *B01J 23/10* (2013.01); *B01J 35/1004* (2013.01); *B01J 35/1038* (2013.01); *B01J 37/08* (2013.01); *C07C 29/157* (2013.01); *C07C 31/04* (2013.01)

(58) Field of Classification Search
CPC ... B01J 23/44; B01J 23/08; B01J 23/10; B01J 35/1004; B01J 35/1038; B01J 37/08; B01J 23/62; B01J 35/002; B01J 35/1014; B01J 35/1061; B01J 37/0018; B01J 23/002; B01J 35/10; B01J 35/1019; B01J 2523/3712;
(Continued)

(56) References Cited

U.S. PATENT DOCUMENTS

2007/0087934 A1* 4/2007 R.M. Martens ......... B01J 29/80
502/64

OTHER PUBLICATIONS

Ye et al (Methanol synthesis from CO2 hydrogenation over a Pd4/In2O3 model catalyst: A combined DFT and kinetic study, Journal of Catalysis, 2014) (Year: 2014).*
(Continued)

*Primary Examiner* — Colin W. Slifka
*Assistant Examiner* — Logan Edward Laclair
(74) *Attorney, Agent, or Firm* — Fox Rothschild LLP

(57) ABSTRACT

Disclosed are a catalyst used for converting carbon dioxide to methanol by hydrogenation and a method preparing the sane. The caratlys may include: a mesoporous indium oxide; and a catalyst supported on the mesoporous indium oxide. Preferably, a porous structure of the mesoporous indium oxide may have Ia3d symmetry and may include mesopores and micropores interconnecting the mesopores.

12 Claims, 10 Drawing Sheets

(51) Int. Cl.
*C07C 29/157* (2006.01)
*C07C 31/04* (2006.01)

(58) Field of Classification Search
CPC ..... C07C 29/157; C07C 31/04; C07C 29/153; C07C 29/149; Y02P 20/52
See application file for complete search history.

(56) References Cited

OTHER PUBLICATIONS

• Frei et al (Atomic-scale engineering of indium oxide promotion by palladium for methanol production via CO2 hydrogenation, Nature Connections, 2019) (Year: 2019).*

Zhao et al (Enhancement of NO2 gas sensing response based on ordered mesoporous Fe-doped In2O3, Sensors and Actuators B: Chemical, 2014) (Year: 2014).*

Chen et al (Cerium-doped indium oxide nanosphere arrays with enhanced ethanol-sensing properties, Journal of Nanoparticle Research, 2019). (Year: 2019.*

K. Sun et al., "Hydrogenation of CO2 to methanol over In2O3 catalyst", Journal of CO2 Utilization, vol. 12, pp. 1-6 (2015).

H. Jiang et al., "Efficient hydrogenation of CO2 to methanol over Pd/In2O3/SBA-15 catalysts", Journal of CO2 Utilization, vol. 36, pp. 33-39 (2020).

O. Martin et al., "Indium Oxide as a Superior Catalyst for Methanol Synthesis by CO2 Hydrogenation", Angew. Chem. Int. Ed., vol. 55, pp. 6261-6265 (2016).

C. Li et al., "Development of highly stable catalyst for methanol synthesis from carbon dioxide", Applied Catalysis A: General, vol. 469, pp. 306-311 (2014).

M.S. Frei et al., "Atomic-scale engineering of indium oxide promotion by palladium for methanol production via CO2 hydrogenation", Nature Communications, https//doi.org/10/10138/s41467-019-11349-0 (www.nature.com/naturecommunications) 2019.

J. Toyir et al., "Highly effective conversion of CO2 to methanol over supported and promoted copper-based catalysts: influence of support and promoter", Applied Catalysis B. Environmental 29, pp. 207-215 (2001).

A. Ota et al., "Comparative study of hydrotalcite-derived supported Pd2Ga and PdZn intermetallic nanoparticles as methanol synthesis and methanol steam reforming catalysts", Journal of Catalysis, vol. 293, pp. 27-38 (2012).

X. Jiang et al., "Bimetallic Pd—Cu catalysts for selective CO2 hydrogenation to methanol", Applied Catalysis B: Environmental 170-171, pp. 173-185 (2015).

X. Liu et al., "Nanocrystalline zirconia as catalyst support in methanol synthesis", Applied Catalysis A: General 279, pp. 241-245 (2005).

J. Toyir et al., "Catalytic performance for CO2 conversion to methanol of gallium-promoted copper-based catalysts: influence of metallic precursors", Applied Catalysis B: Environmental 34, pp. 255-266 (2001).

* cited by examiner

CATALYST FOR CONVERSION OF CARBON DIOXIDE TO METHANOL BY HYDROGENATION, AND METHOD FOR PREPARING THE SAME

CROSS-REFERENCE TO RELATED APPLICATION

This application claims priority to and benefits of Korean Patent Application No. 10-2020-0077601, filed in the Korean Intellectual Property Office on Jun. 25, 2020, the entire contents of which are incorporated herein by reference.

TECHNICAL FIELD

The present invention relates to a catalyst for converting carbon dioxide into methanol by hydrogenation and a method for preparing the same. The catalyst may increase reactivity, stably increase catalytic activity, reduce deactivation, and maintain stability for a long time.

BACKGROUND OF THE INVENTION

It is becoming increasingly important to produce alternative energy due to depletion of fossil fuels. Methanol may be a solution because it has a high hydrogen energy density. For example, methanol is a low-cost, highly efficient, renewable alternative resource because hydrogen can be mass-produced by using fuel cells or the like.

Although methanol can be produced by various methods, a reaction of synthesizing methanol using a synthetic gas including carbon dioxide, a by-product gas of factories and steel mills, has been introduced. This reaction is environment-friendly because it can recycle carbon dioxide, which is a greenhouse gas, and can effectively synthesize methanol, and is evaluated as a very economical process thanks to various uses of methanol. For example, the following reactions occur through hydrogenation of carbon dioxide.

(1) Methanol synthesis reaction (MeOH synthesis): $CO_2 + 3H_2 \rightarrow CH_3OH + H_2O$ (2) Reverse water gas shift reaction (RWGS): $CO_2 + H_2 \rightarrow CO + H_2O$ (3) Methane production reaction: $CO_2 + 4H_2 \rightarrow CH_4 + 2H_2O$ A target product in the three reactions is methanol in the first reaction. Carbon monoxide and methane produced in the other two reactions are byproducts of no value. In order to reduce such by-products, since the reaction uses a metal oxide-based catalyst, it is important to improve a specific surface area of the catalyst and to interact with a cocatalyst. To this end, it is the most important issue to introduce a material that prevents agglomeration while ideally improving the non-surface area, and to find a cocatalyst material that can improve reactivity and synthesize it at an optimal ratio.

The above information disclosed in this Background section is only for enhancement of understanding of the background of the invention, and therefore it may contain information that does not form the prior art that is already known in this country to a person of ordinary skill in the art.

SUMMARY

In preferred aspects, provided are a catalyst for conversion of carbon dioxide to methanol by hydrogenation and a method of preparing the same. The catalyst as described herein may increase reactivity by increasing a mesoporous structure to increase a specific surface area, maintain the mesoporous structure well to stably increase catalytic activity even when the reactivity is further increased by including additional catalyst (e.g., secondary catalyst), and reduce deactivation because the catalyst is not well aggregated and maintaining stability for a long time.

In an aspect, provided is a catalyst for converting carbon dioxide into methanol, e.g., by hydrogenation. The catalyst may include mesoporous indium oxide; and a secondary catalyst suitably supported on the mesoporous indium oxide. Preferably, a porous structure of the mesoporous indium oxide may be Ia3d symmetry which may include mesopores and micropores interconnecting the mesopores.

A term "mesopores" as used herein refers to a porous structure or plurality of pores having the diameter between 2 nm and 50 nm according to International Union of Pure and Applied Chemistry (IUPAC) nomenclature, however, the size of the mesopores may fall in a range of 1 nm to 100 nm. A term "micropores" as used herein refers to a porous structure or plurality of pores having the diameter less than about 2 nm according to IUPAC nomenclature, however, the size of the micropores may be less than the size of the mesopores used and described herein.

A term "Ia3d symmetry" is understood as a kind of space group, which classifies symmetries of a crystal in space usually in three dimensions such as cubic crystal system. The Ia3d symmetry has a point group of the unit cell as understood and defined by International Tables for Crystallography (or International Short Symbol), and for example, in Ia3d symmetry, three sides of the cells are in same length at right angles each other.

The mesoporous indium oxide may have a specific surface area of greater than about 40 $m^2/g$, and a pore volume thereof may be greater than about 0.05 $cm^3/g$.

The mesoporous indium oxide may have a particle size of about 15 nm to 20 nm and a size of the mesopores may range from about 2 nm to 20 nm.

The mesoporous indium oxide may be formed using a mesoporous silica template (e.g., KIT-6).

In one aspect, the catalyst may include for example any of palladium (Pd), cerium oxide ($CeO_2$), gallium oxide ($Ga_2O_3$), or a combination thereof.

In an aspect, the catalyst may suitably include an amount of about 1 wt % to 9 wt % of the palladium catalyst with respect to the total weight of the catalyst.

In an aspect, the catalyst may suitably include an amount of about 1 wt % to 5 wt % of the cerium oxide or the gallium oxide secondary catalyst with respect to the total weight of the catalyst.

In an aspect, provided is a method of preparing a catalyst, which may be used for converting carbon dioxide into methanol by hydrogenation. The method may include supporting a precursor of an indium oxide on a mesoporous silica template; preparing a mesoporous indium oxide by separating the mesoporous silica template from the precursor of the indium oxide is supported; and supporting a secondary catalyst on the mesoporous indium oxide.

The supporting of the precursor may be performed by preparing a first solution including the precursor of the indium oxide and contacting the first solution with the mesoporous silica template.

The first solution containing the precursor of the indium oxide may include an amount of about 5 wt % to 10 wt % of the indium oxide precursor with respect to the total weight of the first solution.

The supporting of the precursor may be performed by first drying the first solution solution and the mesoporous silica template on which the precursor of the indium oxide is supported at a temperature of about 20° C. to 30° C., second drying at a temperature of about 60° C. to 90° C., and firing at a temperature of about 300° C. to 550° C. As referred to herein, the term solution includes dispersions and other admixtures as well as true solutions.

In the supporting of the precursor, the first solution may include the precursor of the indium oxide in an amount of about 3 parts by weight to 5 parts by weight with respect to 1 part by weight of the mesoporous silica template.

Alternatively, the preparing of the mesoporous indium oxide may be performed by adding the mesoporous silica template on which the precursor of the indium oxide is supported into an alkaline aqueous solution, and reacting them at a temperature of about 70° C. to 90° C. for about 2 to 4 h.

The supporting of the catalyst may be performed by preparing a second solution including a precursor of the catalyst and contacting the second solution with the mesoporous indium oxide.

The second solution containing the precursor of the catalyst may include an amount of about 1 wt % to 9 wt % of the precursor with respect to the total weight of the second solution.

The supporting of the s catalyst may be performed by drying the second solution and the mesoporous indium oxide on which the secondary precursor is supported at a temperature of about 60° C. to 90° C. and firing at a temperature of about 300° C. to 550° C.

According to various exemplary embodiments, the catalyst for conversion of carbon dioxide to methanol by hydrogenation may increase reactivity by increasing a mesoporous structure to increase a specific surface area, maintain the mesoporous structure well to stably increase catalytic activity even when the reactivity is further increased by including a catalyst, and reduce deactivation because the catalyst is not well aggregated and maintaining stability for a long time.

DETAILED DESCRIPTION

Figure 1:
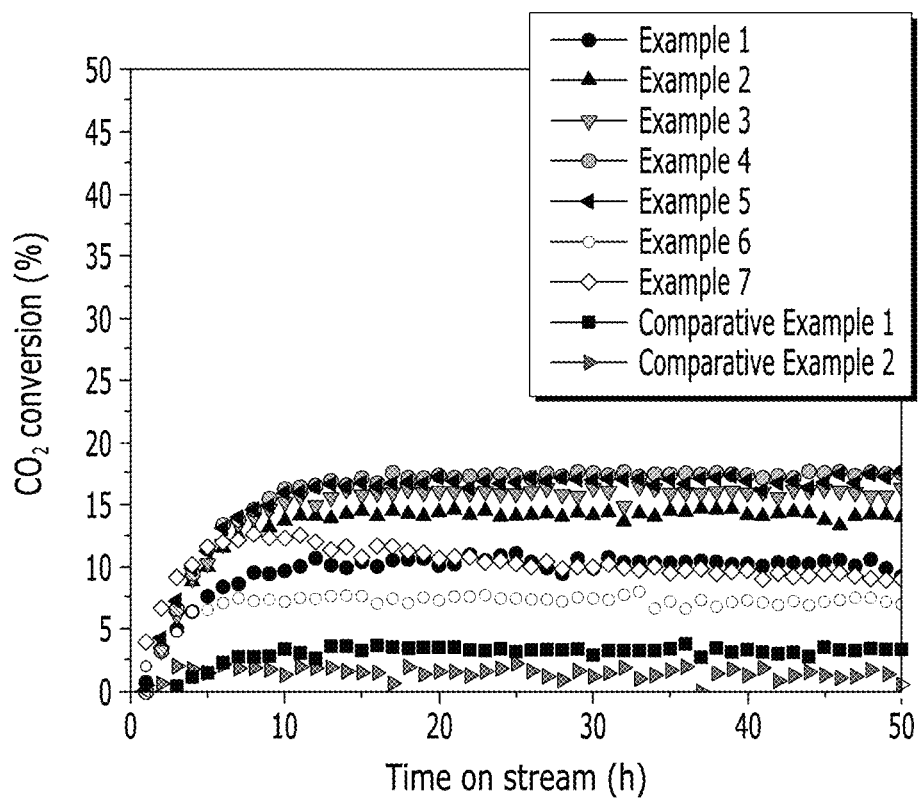
FIG. 1 and FIG. 2 shows graphs showing hydrogenation results of carbon dioxide for each exemplary catalyst in Experimental Example 2.

The advantages and features of the present invention and the methods for accomplishing the same will be apparent from the exemplary embodiments described hereinafter with reference to the accompanying drawings. However, an implemented form may not be limited to exemplary embodiments disclosed below. Unless otherwise defined, all terms (including technical and scientific terms) used herein have the same meaning as commonly understood by one of ordinary skill in the art. In addition, terms defined in commonly used dictionary are not to be ideally or excessively interpreted unless explicitly defined.

In addition, throughout the specification unless explicitly described to the contrary, the word "comprise" and variations such as "comprises" or "comprising" will be understood to imply the inclusion of stated elements but not the exclusion of any other elements.

Further, as used herein, the singular forms "a", "an", and "the" are intended to include the plural forms as well, unless the context clearly indicates otherwise.

Unless otherwise indicated, all numbers, values, and/or expressions referring to quantities of ingredients, reaction conditions, polymer compositions, and formulations used herein are to be understood as modified in all instances by the term "about" as such numbers are inherently approximations that are reflective of, among other things, the various uncertainties of measurement encountered in obtaining such values.

Further, unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

A catalyst used for converting carbon dioxide into methanol by hydrogenation according to an exemplary embodiment of the present invention may include a primary catalyst including a mesoporous indium oxide, and a catalyst supported on the mesoporous indium oxide.

In general, a fired commercial indium oxide powder or a bulk indium oxide obtained by firing an indium hydroxide is used as an indium-based catalyst. Such a catalyst is easy to synthesize and easy to obtain. However, because of the bulk state, a specific surface area is small and a possibility of clumping and an amount entering a reactor may be limited.

On the other hand, unlike the bulk indium oxide, the mesoporous indium oxide has a large specific surface area so as to increase reactivity and to prevent agglomeration of a catalyst, thereby reducing deactivation and maintaining stability.

The mesoporous indium oxide may have a reversed phase of a mesoporous structure of a mesoporous silica template (e.g., KIT-6). That is, a porous structure of the mesoporous indium oxide may have Ia3d symmetry, and for example, have a bicontinuous cubic network structure including mesopores and micropores interconnecting the mesopores. Since the mesoporous indium oxide prepared in this way has a mesopore structure inside an indium oxide compared to a bulk indium oxide, it can maximize an active point of the indium oxide, which is an active material, because it has a large specific surface area compared with a weight of the catalyst. In addition, since a catalyst can be supported inside the pore, a contact area between the catalyst and the indium oxide may be widened and an amount of the supported catalyst may be increased, thereby greatly improving performance of the catalyst through a synergistic effect.

Accordingly, the mesoporous indium oxide may have a specific surface area of about 40 $m^2$/g, e.g. about 40 $m^2$/g to 120 $m^2$/g. When the specific surface area of the mesoporous indium oxide is less than about 40 $m^2$/g, a number of active sites of the indium oxide may be small, and the amount of the catalyst that can be supported is limited, so that a small amount of conversion of $CO_2$ may be made.

The mesoporous indium oxide may have a pore volume of greater than about 0.05 $cm^3$/g, e.g., 0.05 $cm^3$/g to 0.3 $cm^3$/g. When the pore volume of the mesoporous indium oxide is greater than about 0.05 $cm^3$, it may be difficult to support the catalyst inside the pore, and dispersibility thereof may be low.

The mesoporous indium oxide may have a particle size of about 15 nm to 20 nm, e.g., about 17 nm to 18 nm. When the particle size of the mesoporous indium oxide is less than about 15 nm, mesoporous indium oxide particles may be formed to be small, thereby not maintaining the mesoporous structure during a reaction thereof. When it is greater than about 20 nm, bulk indium oxide particles may be excessively generated.

The mesopores in the mesoporous indium oxide may have a size ranging from about 2 nm to 50 nm, e.g., from about 2 nm to 20 nm, or from about 6 nm to 9 nm. When mesopores of the mesoporous indium oxide have a size of less than about 2 nm, the size of the pores may be too small, thereby reducing a material transfer into an inner surface of the indium oxide of which a reactant is an active material, and the catalyst may not be supported even into the pores as described above. When the pore size is greater than about 50 nm, the structure of the indium oxide may be formed in bulk, so the dispersibility of the indium oxide may be low, and the amount of the catalyst supported may be limited.

The catalyst is supported on the mesoporous indium oxide. The s catalyst may stably increase catalytic activity by maintaining the mesoporous structure well without being broken while further increasing the reactivity of the mesoporous indium oxide.

The catalyst may include palladium (Pd), cerium oxide ($CeO_2$), gallium oxide ($Ga_2O_3$), or a combination thereof.

The catalyst may include an amount of about 1 wt % to 9 wt %, e.g., 7 wt % to 9 wt %, of a palladium catalyst with respect to the total weight of the catalyst. When a content of the palladium catalyst is less than about 1 wt %, the synergistic effect with the indium oxide may not appear, and when it is greater than about 9 wt %, larger palladium particles may be formed so as to reduce $CO_2$ conversion performance.

The catalyst may include an amount of about 1 wt % to 9 wt %, e.g., about 3 wt % to 7 wt %, of a cerium oxide or gallium oxide catalyst with respect to the total weight of the catalyst. When a content of the cerium oxide or the gallium oxide catalyst is less than about 1 wt %, a promoting effect of the catalyst may not appear, and when it is greater than about 9 wt %, total activity of the catalyst may be reduced due to the reduced content of the indium oxide.

A method of preparing a catalyst for conversion of carbon dioxide to methanol by hydrogenation according to an exemplary embodiment of the present invention may include: supporting a precursor of an indium oxide on a mesoporous silica template (e.g., KIT-6); preparing a mesoporous indium oxide by separating the mesoporous silica template from the precursor of the indium oxide is supported; and supporting a catalyst on the mesoporous indium oxide.

The method of preparing the catalyst, which is a method capable of maximizing a specific surface area, a dispersion degree, and efficiency of an indium oxide-based catalyst, may provide a catalyst with high activity and stability in a methanol synthesis reaction through hydrogenation of carbon dioxide at a high temperature by preparing a mesoporous indium oxide catalyst having a high specific surface area and high dispersion and supporting a catalyst thereon.

The supporting of the precursor may be performed by preparing a first solution including the precursor of the indium oxide and contacting the first solution with the mesoporous silica template.

The precursor of the indium oxide may include an indium nitrate, an indium hydroxide, an indium chloride, an indium sulfate, or a hydrate thereof, or a combination thereof.

The first solution containing the precursor of the indium oxide may be prepared by injecting the precursor of the indium oxide into a solvent, and the solvent may contain distilled water, ethanol, methanol, ethylene glycol, propylene glycol, isopropyl alcohol, or a combination thereof.

The first solution containing the precursor of the indium oxide may include an amount of about 5 wt % to 10 wt %, e.g., about 6 wt % to 8 wt %, of the indium oxide precursor with respect to the total weight of the first solution. When the precursor content of the indium oxide is less than about 5 wt % with respect to the total weight of the first solution, the indium precursor solution may not be supported inside the pores of KIT-6, and when it is greater than about 10 wt %, a lot of indium nitrate accumulates outside the pores of KIT-6, and thus it may increase the relative amount of bulk indium oxide rather than having a mesoporous structure.

The supporting of the precursor may be performed by first drying the first solution containing the mesoporous silica template on which the precursor of the indium oxide is supported at a temperature of about 20° C. to 30° C., second drying it at a temperature of about 60° C. to 90° C., and firing them at a temperature of about 300° C. to 550° C.

In the supporting of the precursor, a reason why the solution containing the mesoporous silica template on which the precursor of the indium oxide is supported is first dried at 20° C. to 30° C. and second dried at 60° C. to 90° C. is for adjusting a drying rate to easily introduce the indium oxide precursor into the pores of KIT-6 during the first drying, and to remove only a residual solvent (e.g., water) during the second drying.

In the supporting of the precursor, when a firing temperature is less than about 300° C., it may be difficult to convert to indium oxide due to decomposition of the indium precursor, and when it is greater than about 550° C., the particle size of the generated indium oxide may be too large or the mesoporous structure may collapse.

In the supporting of the precursor, the first solution may include of the precursor of the indium oxide in an amount of about 3 parts by weight to 5 parts by weight, e.g., about 3.5 parts by weight to 4.5 parts by weight, with respect to 1 part by weight of the mesoporous silica template. When the content of the precursor of the indium oxide is less than about 3 parts by weight with respect to 1 part by weight of the mesoporous silica template, the particle size of the mesoporous indium oxide may be too small as the indium oxide precursor cannot be introduced into the pores of KIT-6. When it is greater than about 5 parts by weight, the indium oxide precursor may be supported on the outside of the pores during a KIT-6 support process, thereby increasing a relative amount of the bulk indium oxide.

Alternatively, the preparing of the mesoporous indium oxide may be performed by adding the mesoporous silica template on which the precursor of the indium oxide is supported and a strong alkaline aqueous solution such as NaOH, and reacting them at a temperature of about 70° C. to 90° C. for about 2 to 4 h.

In the preparing of the mesoporous indium oxide, when the reaction temperature is less than about 70° C., the KIT-6 template may not be properly removed, and thus the content of indium oxide in the obtained catalyst may be low, thereby reducing $CO_2$ conversion activity. When it is greater than about 90° C., the indium oxide formed inside the pores of KIT-6 may be removed together with KIT-6. When a reaction time is less than about 2 h, KIT-6 may not be sufficiently removed, and when it is greater than about 4 h, the indium oxide formed inside the pores of KIT-6 may be removed together with KIT-6.

When a hydrogen fluoride is used instead of the strong alkaline aqueous solution, it may dissolve the oxide as well as KIT-6, and thus the indium oxide is likely to be removed as well, and silica may not be removed well in other weakly acidic or weakly alkaline solutions.

The supporting of the catalyst may be performed by preparing a second solution containing a secondary precursor of the catalyst and contacting the second solution with the mesoporous indium oxide.

The secondary precursor of the catalyst may include a palladium nitrate, a palladium hydroxide, a palladium acetate, a palladium chloride, a cerium nitrate, a cerium hydroxide, a cerium chloride, a gallium nitrate, a gallium hydroxide, a gallium chloride, a hydrate thereof, or a combination thereof.

The second solution including the secondary precursor of the catalyst may be prepared by injecting the secondary precursor of the catalyst into a solvent, and the solvent may contain distilled water, ethanol, methanol, ethylene glycol, propylene glycol, isopropyl alcohol, or a combination thereof.

The second solution containing the secondary precursor of the catalyst may include an amount of about 1 wt % to 9 wt %, e.g., about 7 wt % to 9 wt %, of the catalyst precursor with respect to the total weight of the second solution. When the second precursor content of the catalyst is less than about 1 wt %, the synergistic effect with the indium oxide may not appear, and when it is greater than about 9 wt %, larger catalyst particles may be formed so as to reduce $CO_2$ conversion performance.

The supporting of the catalyst may be performed by drying the second solution and the mesoporous indium oxide on which the secondary precursor of the catalyst is supported at a temperature of about 60° C. to 90° C. and firing it at a temperature of about 300° C. to 550° C.

In the supporting of the catalyst, when the drying temperature is less than about 60° C., the indium oxide may leak out of the pores during the firing process as all the solvent is not removed, while when it is greater than about 90° C., the drying rate may be too fast, so the indium oxide may leak out of the pores during drying as described above.

In the third step, when the firing temperature is less than about 300° C., the catalyst may not change from a precursor form to an oxide form, while when it is greater than about 500° C., particles of the catalyst in the form of oxide may be largely formed, which may deviate from the porous structure of the mesoporous indium oxide or may collapse the structure.

In one aspect, the present invention relates to mesoporous indium oxide catalyst, supporting a secondary catalyst used for a methanol synthesis reaction through hydrogenation of carbon dioxide to prepare methanol by reacting carbon dioxide, which is a main component of a greenhouse gas, and hydrogen, and a method for preparing the same. As such, reactivity of a hydrogenation reaction of carbon dioxide may be improved through a synergistic effect of the secondary catalyst and an indium oxide by synthesizing a mesoporous indium oxide by wet support using mesoporous KIT-6 with a high specific surface area, and thus, dry supporting palladium, a cerium oxide, or a gallium oxide, which is a secondary catalyst.

The mesoporous indium oxide catalyst prepared by the method disclosed in the present invention may have a greater specific surface area and prevents agglomeration compared to the bulk indium oxide prepared through a general method, and accordingly, when the secondary catalyst is supported, reaction activity may be significantly greater than that of the bulk indium oxide. Accordingly, it exhibits an excellent carbon dioxide conversion rate, methanol selectivity, and reaction stability, and thus may be used as a catalyst for methanol preparing and carbon dioxide reduction under a high temperature catalytic reaction condition.

EXAMPLE

Hereinafter, specific examples of the invention are described. However, the examples described below are for illustrative purposes only, and the scope of the invention is not limited thereto.

Comparative Example 1: Preparing of m-$In_2O_3$ (1) Preparing of KIT-6

18 g of a Pluronic P123 copolymer (poly(ethylene oxide)-poly(propylene oxide)-poly(ethylene oxide), Sigma-Aldrich, hereinafter referred to as P123) was dissolved overnight in 150 ml of distilled water by strong stirring at room temperature. In addition, 32 ml of hydrochloric acid (37%) and 500 ml of distilled water were separately provided by stirring them for 10 minutes or more at a temperature of 35° C. When all of the P123 was dissolved to become a transparent solution, a P123 aqueous solution was added into a hydrochloric acid aqueous solution, stirred for 10 minutes, and then 18 g of 1-butanol was added and stirred for 1 h. Thereafter, 38.7 g of tetraethyl orthosilicate ((Sigma-Aldrich), hereinafter referred to as TEOS) was rapidly added and stirred for 24 h while maintaining the temperature at 35° C. Thereafter, the mixture was transferred to a hydrothermal reactor, and hydrothermal reaction was performed in an oven at a temperature of 110° C. for 25 h. A prepared white solid product was filtered and washed with distilled water, and then was dried in a convection oven at a temperature of 110° C. for 30 min, and thereafter, was fired at a temperature of 550° C. for 6 h at a heating speed of 1° C./min in an air atmosphere.

(2) Preparing of Mesoporous Indium Oxide (m-In$_2$O$_3$)

A mesoporous indium oxide was prepared through wet supporting and template removal on a KIT-6 support.

First, the wet supporting was performed by making a solution by mixing 3 g of indium(III) nitrate hydrate (99.99%, Alfa Aesar, hereinafter referred to as In(NO$_3$)$_3$·xH$_2$O) and 40 ml of distilled water, adding it into 0.75 g of KIT-6 to mix it well, and stirring it at room temperature for 2 h. It was stirred, and then was dried at room temperature overnight to evaporate, and then dried in a convection oven at a temperature of 80° C. for about two days so that the distilled water is blown away. After complete drying and firing at a temperature of 300° C. for 2 h, a mesoporous indium oxide supported on KIT-6 was prepared.

Next, the template removal was a process of removing KIT-6 from the synthesized material. 200 ml of a 2 M NaOH solution was provided and heated to a temperature of 80° C. by using a heating mantle. When it reached a temperature of 80° C., the mesoporous indium oxide supported on KIT-6 was added and stirred for 3 h. It was stirred, and then washed twice with distilled water and ethanol while being filtered, and was dried in the convection oven at a temperature of 80° C. overnight. This operation was identically performed one more time. The prepared catalyst was called m-In$_2$O$_3$.

Example 1: Preparing of Pd(1)/m-In$_2$O$_3$

A catalyst was prepared by dry supporting a secondary catalyst on an m-In$_2$O$_3$ catalyst prepared in Comparative Example 1.

0.5 g of prepared m-In$_2$O$_3$ was provided and dried in an oven at a temperature of 80° C. for 30 min to boil off water. 0.011 g of palladium(II) nitrate hydrate (99.8%, Alfa Aesar, hereinafter referred to as Pd(NO$_3$)$_2$·xH$_2$O) calculated using 1 wt % of palladium compared with m-In$_2$O$_3$ was provided and dissolved in 0.1 ml of distilled water.

After it was dissolved, it was extracted with a pipette, dripped dropwise into a dried mesoporous indium oxide, and rubbed with a spoon to be mixed well. This operation was repeated until the solution in the pipette was used up. After the dry support was finished, it was put in the oven at a temperature of 80° C. and dried overnight, and then was fired at a temperature of 300° C. for 3 h to prepare a catalyst, which is was called Pd(1)/m-In$_2$O$_3$.

Example 2: Preparing of Pd(3)/m-In$_2$O$_3$

Example 2 was performed in a same manner as in Example 1, but 0.033 g of Pd(NO$_3$)$_2$·xH$_2$O was used by calculating a palladium content as 3 wt % compared with m-In$_2$O$_3$. Other catalyst preparing procedures were the same as in Example 1.

Example 3: Preparing of Pd(5)/m-In$_2$O$_3$

Example 3 was performed in a same manner as in Example 1, but 0.054 g of Pd(NO$_3$)$_2$·xH$_2$O) was used by calculating a palladium content as 5 wt % compared with m-In$_2$O$_3$. Other catalyst preparing procedures were the same as in Example 1.

Example 4: Preparing of Pd(7)/m-In$_2$O$_3$

Example 4 was performed in a same manner as in Example 1, but 0.076 g of Pd(NO$_3$)$_2$·xH$_2$O) was used by calculating a palladium content as 7 wt % compared with m-In$_2$O$_3$. Other catalyst preparing procedures were the same as in Example 1.

Example 5: Preparing of Pd(9)/m-In$_2$O$_3$

Example 5 was performed in a same manner as in Example 1, but 0.098 g of Pd(NO$_3$)$_2$·xH$_2$O) was used by calculating a palladium content as 9 wt % compared with m-In$_2$O$_3$. Other catalyst preparing procedures were the same as in Example 1.

Comparative Example 2: Preparing of Pd(7)/m-In$_2$O$_3$

Comparative Example 2 was performed in a same manner as in Example 1, but KIT-6(SiO$_2$) was used instead of m-In$_2$O$_3$, and 0.076 g of Pd(NO$_3$)$_2$·xH$_2$O) was used by calculating a palladium content as 7 wt % compared with KIT-6. Other catalyst preparing procedures were the same as in Example 1.

Example 6: Preparing of CeO$_2$(3)/m-In$_2$O$_3$)

A catalyst was prepared by dry supporting a secondary catalyst on an m-In$_2$O$_3$ catalyst prepared in Comparative Example 1.

0.5 g of prepared m-In$_2$O$_3$ was provided and dried in an oven at a temperature of 80° C. for 30 min to boil off water. 0.038 g of cerium(III) nitrate hexahydrate (99%, Sigma-Aldrich, hereinafter referred to as Ce(NO$_3$)$_3$·6H$_2$O) calculated using 1 wt % of cerium oxide compared with m-In$_2$O$_3$ was provided and dissolved in 0.1 ml of distilled water. After it was dissolved, it was extracted with a pipette, dripped dropwise into a dried mesoporous indium oxide, and rubbed with a spoon to be mixed well. This operation was repeated until the solution in the pipette was used up. After the dry support was finished, it was put in the oven at 80° C. and dried overnight, and then was fired at a temperature of 500° C. for 2 h to prepare a catalyst, which was called Ce(3)/m-In$_2$O$_3$.

Example 7: Preparing of Ga$_2$O$_3$(3)/m-In$_2$O$_3$)

A catalyst was prepared by dry supporting a secondary catalyst on an m-In$_2$O$_3$ catalyst prepared in Comparative Example 1.

0.5 g of prepared m-In$_2$O$_3$ was provided and dried in an oven at a temperature of 80° C. for 30 min to boil off water. 0.041 g of Gallium(III) nitrate hydrate (99.9%, Alfa Aesar, hereinafter, referred to as Ga$_2$O$_3$·xH$_2$O) calculated using 3 wt % of gallium oxide compared with m-In$_2$O$_3$ was provided and dissolved in 0.1 ml of distilled water. After it was melted, it was extracted with a pipette, dripped dropwise into a dried mesoporous indium oxide, and rubbed with a spoon to be mixed well. This operation was repeated until the solution in the pipette was used up. After the dry support was finished, it was put in the oven at a temperature of 80° C. and dried overnight, and then was fired at a temperature of 400° C. for 2 h to prepare a catalyst, which was called Ga$_2$O$_3$(3)/m-In$_2$O$_3$.

Experimental Example 1: Experiment for Each Reaction Temperature for Hydrogenation of Carbon Dioxide A hydrogenation experiment of a carbon dioxide was carried out in a ⅜ in Inconel fixed bed reactor. It was carried out based on only a catalyst supporting 3 wt % of a secondary catalyst. 0.20 g of the catalyst was charged, and 5 vol % of $H_2/N_2$ gas was allowed to flow at a space velocity of SV=5000 ml/$g_{cat}$·h before a reaction, and a temperature thereof was raised to a temperature of 300° C. at 5° C./min and reduced for 5 h. Then, the reaction was carried out by injecting a reactive gas having a ratio of carbon dioxide:hydrogen:nitrogen (internal standard material)=24:72:4 at a space velocity of SV=8000 ml/$g_{cat}$·h. The reaction was carried out at four temperatures of 280° C., 300° C., 320° C., and 340° C., each for 20 h.

Specifically, the hydrogenation of the carbon dioxide was tested for activity through an experiment for each temperature for 20 h by using the prepared catalyst (Example 2, Example 6, and Example 7), and these are summarized in Table 1.

Experimental Example 2: Experiment for Each Reaction Catalyst for Hydrogenation of Carbon Dioxide Experimental Example 2 was performed in a same manner as in Experimental Example 1, but may be performed for 50 h at a temperature that shows a highest activity in the results of Experimental Example 1 as a reaction condition.

Figure 2:
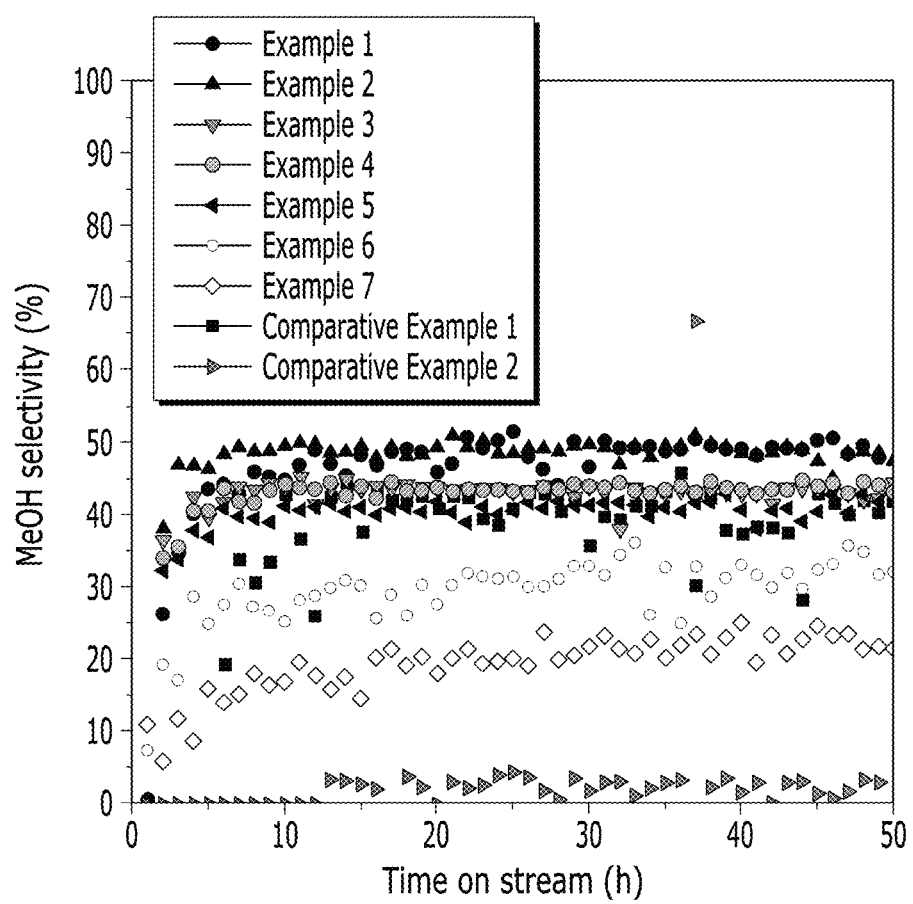

Specifically, the hydrogenation of the carbon dioxide was tested for activity through an experiment for each catalyst for 50 h at the temperature that shows best activity based on the experiment results for each temperature for the hydrogenation of the carbon dioxide by using the prepared catalyst (Examples 1 to 7 and Comparative Examples 1 and 2), and these are summarized in FIG. 1, FIG. 2, and Table 2.

TABLE 1

| Division | Catalyst | Temperature (° C.) | Conversion rate [$CO_2$] (mol %) | Selectivity [MeOH] (mol %) | Selectivity [CO] (mol %) | Selectivity [$CH_4$] (mol %) | MeOH Generation speed (C-mmol/ $g_{cat}$·h) | CO Generation speed (C-mmol/ $g_{cat}$·h) | Production of MEOH (MeOH g/ $kg_{cat}$·h) |
|---|---|---|---|---|---|---|---|---|---|
| Example 2 | Pd(3)/ m-$In_2O_3$ | 280 | 11.0 | 35.4 | 60.7 | 3.6 | 3.7 | 5.8 | 118.6 |
| | | 300 | 15.7 | 28.5 | 67.6 | 3.5 | 3.8 | 9.1 | 121.9 |
| | | 320 | 16.8 | 15.8 | 82.0 | 1.9 | 2.3 | 11.8 | 72.7 |
| | | 340 | 19.8 | 7.4 | 92.1 | 0.4 | 1.2 | 15.6 | 39.5 |
| Example 16 | $CeO_2$(3)/ m-$In_2O_3$ | 280 | 2.0 | 39.0 | 60.5 | 0.5 | 0.6 | 1.1 | 20.5 |
| | | 300 | 4.4 | 38.0 | 60.9 | 1.0 | 1.5 | 2.2 | 48.7 |
| | | 320 | 7.7 | 35.6 | 62.7 | 1.7 | 2.3 | 4.2 | 74.8 |
| | | 340 | 11.4 | 21.9 | 76.3 | 1.8 | 2.1 | 7.5 | 67.5 |
| Example 17 | $Ga_2O_3$(3)/ m-$In_2O_3$ | 280 | 4.0 | 21.4 | 78.2 | 0.4 | 1.0 | 2.5 | 30.5 |
| | | 300 | 8.1 | 27.2 | 71.8 | 0.9 | 1.9 | 5.0 | 61.0 |
| | | 320 | 11.8 | 20.2 | 78.7 | 1.1 | 2.0 | 8.0 | 65.1 |
| | | 340 | 13.9 | 13.2 | 85.9 | 0.9 | 1.6 | 10.2 | 50.1 |

As shown in Table 1, in the case of a palladium supported catalyst, production of MeOH was similarly highest at a temperature of 280° C. and 300° C., but considering that a CO generation speed was low at a temperature of 280° C., the activity was the best at the temperature of 280° C. The cerium oxide and gallium oxide supported catalysts showed best activity at a temperature of 320° C.

TABLE 2

| Division | Catalyst | Temperature | Conversion rate [$CO_2$] (mol %) | Selectivity [MeOH] (mol %) | Selectivity [CO] (mol %) | Selectivity [$CH_4$] (mol %) |
|---|---|---|---|---|---|---|
| Example 1 | Pd(1)/ m-$In_2O_3$ | 280 | 9.6 | 46.2 | 53.6 | 0.3 |
| Example 2 | Pd(3)/ m-$In_2O_3$ | | 13.3 | 43.9 | 56.1 | 0.0 |
| Example 3 | Pd(5)/ m-$In_2O_3$ | | 14.7 | 44.0 | 56.0 | 0.0 |
| Example 4 | Pd(7)/ m-$In_2O_3$ | | 16.0 | 44.2 | 55.8 | 0.0 |
| Example 5 | Pd(9)/ m-$In_2O_3$ | | 15.6 | 44.3 | 55.7 | 0.0 |
| Example 6 | Pd(3)/ m-$In_2O_3$ | 320 | 7.1 | 29.4 | 69.2 | 1.4 |
| Example 7 | $Ga_2O_3$(3)/ m-$In_2O_3$ | 320 | 10.2 | 19.4 | 80.1 | 0.5 |
| Comparative Example 1 | m-$In_2O_3$ | 280 | 3.0 | 36.1 | 63.5 | 0.4 |
| Comparative Example 2 | Pd(7)/$SiO_2$ | | 1.5 | 2.9 | 45.1 | 52.0 |

As shown in FIG. 1, FIG. 2, and Table 2, when the secondary catalyst was supported, the activity was much better than that of m-In$_2$O$_3$, and the palladium supported catalyst showed best activity at 7 wt %. Since the palladium supported catalyst was superior to the cerium oxide and gallium oxide supported catalysts, and the palladium silica catalyst had little activity, it was determined that the activity was excellent by a synergistic effect of the palladium and the indium oxide. The cerium oxide and gallium oxide supported catalysts also exhibit improved activity by a synergistic effect with indium oxide.

Experimental Example 3: X-Ray Diffraction Pattern (XRD) Analysis

X-ray diffraction pattern analysis was performed to check formation of mesopores and crystallinity of the prepared catalysts of Pd/m-In$_2$O$_3$, CeO$_2$/m-In$_2$O$_3$, and Ga$_2$O$_3$/m-In$_2$O$_3$.

Figure 3:
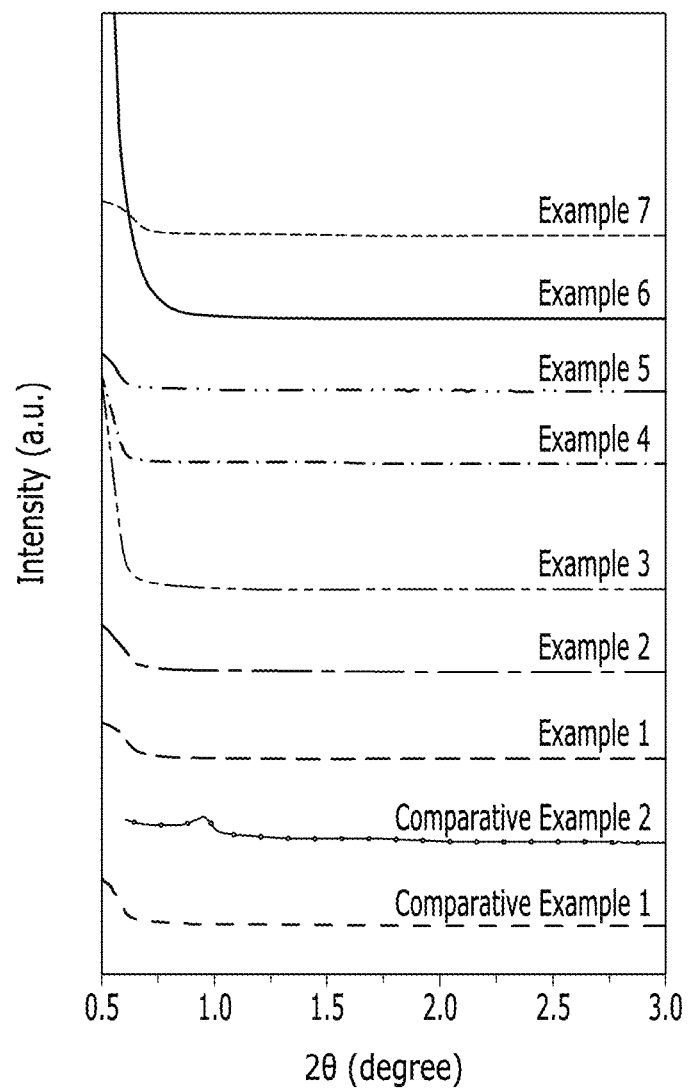
FIG. 3 and FIG. 4 shows graphs showing the results of analyzing X-ray diffraction patterns of exemplary catalysts in Experimental Example 3.
Figure 4:
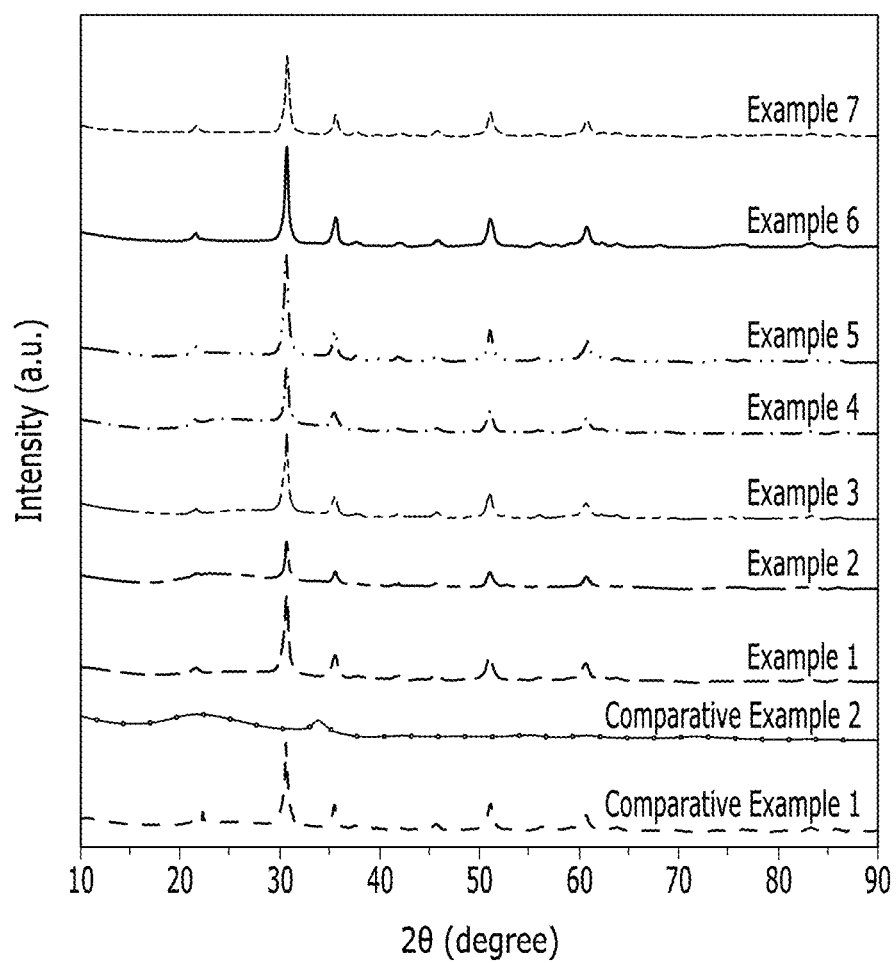

Specifically, an X-ray diffraction pattern was analyzed to determine whether the prepared catalysts (Examples 1 to 7 and Comparative Examples 1 and 2) were synthesized in a mesoporous structure and to check crystallinity, and results thereof are shown in FIG. 3 and FIG. 4.

As shown in FIG. 3 and FIG. 4, a peak that bends at a small angle (0.5 to 3.0 degrees) indicates a mesoporous structure, and a peak of m-In$_2$O$_3$ is indicated at a large angle (10 to 90 degrees), to thereby maintain the crystallinity.

Experimental Example 4: Transmission Electron Microscopy (TEM) Analysis

Figure 5:
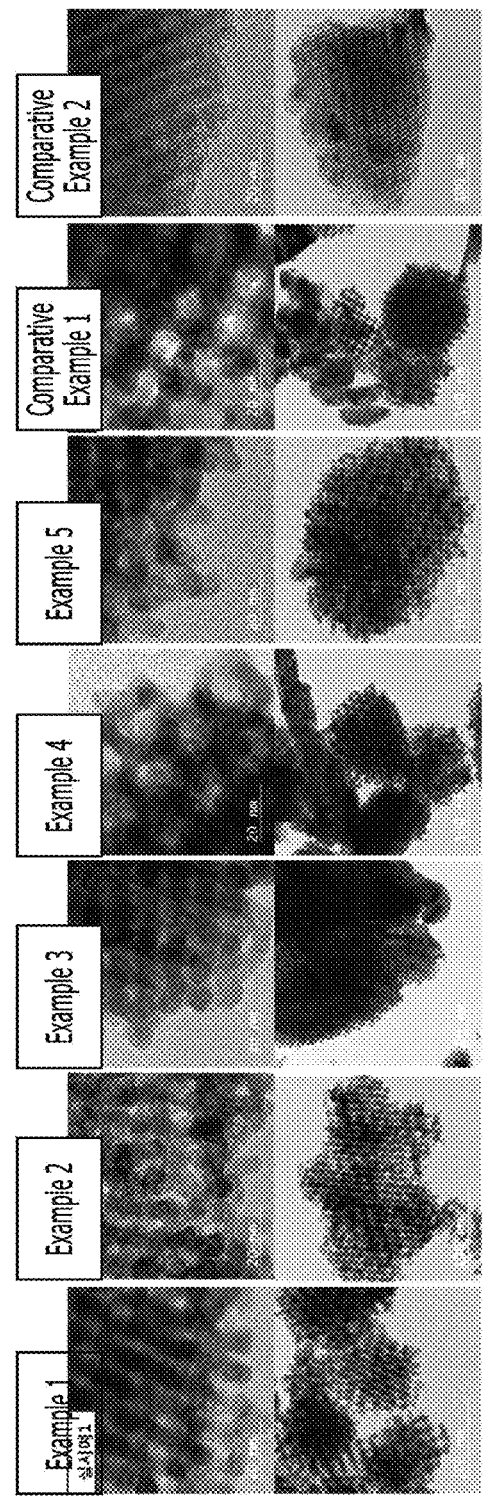
FIG. 5 shows a photograph showing a result of a transmission electron microscope (TEM) analysis of an exemplary catalyst in Experimental Example 4.

Images of the prepared catalysts of Pd/m-In$_2$O$_3$, CeO$_2$/m-In$_2$O$_3$, and Ga$_2$O$_3$/m-In$_2$O$_3$ were acquired through TEM analysis, and results thereof are shown in FIG. 5.

As shown in FIG. 5, in the case of the palladium supported catalyst, the mesoporous structure was well maintained compared with m-In$_2$O$_3$, and secondary catalysts were supported in the pore. In the case of palladium silica, the mesoporous structure was weaker and the crystallinity was reduced compared with the palladium indium oxide. Accordingly, m-In$_2$O$_3$ had better mesoporous and crystal structures compared with KIT-6.

Experimental Example 5: Energy Dispersive X-Ray Spectroscopy (EDS) and X-Ray Fluorescence (XRF) Analysis Energy dispersive X-ray spectroscopy (EDS) analysis and X-ray fluorescence (XRF) analysis were performed to check a secondary catalyst content and a dispersion degree of the prepared catalyst of Pd/m-In$_2$O$_3$, CeO$_2$/m-In$_2$O$_3$, and Ga$_2$O$_3$/m-In$_2$O$_3$. Results thereof are shown in FIG. 6 and Table 3.

TABLE

| Division | Analysis method Catalyst | XRF Pd/Si (concentration ratio) | EDS PdO/m-In$_2$O$_3$ (% by mass) |
|---|---|---|---|
| Example 1 | Pd(1)/m-In$_2$O$_3$ | 1.18/0.12 | 0.0 |
| Example 2 | Pd(3)/m-In$_2$O$_3$ | 2.56/0.09 | 6.3 |
| Example 3 | Pd(5)/m-In$_2$O$_3$ | 2.97/0.09 | 0.0 |
| Example 4 | Pd(7)/m-In$_2$O$_3$ | 5.37/0.10 | 23.6 |
| Example 5 | Pd(9)/m-In$_2$O$_3$ | 5.71/0.08 | 7.7 |

Figure 6:
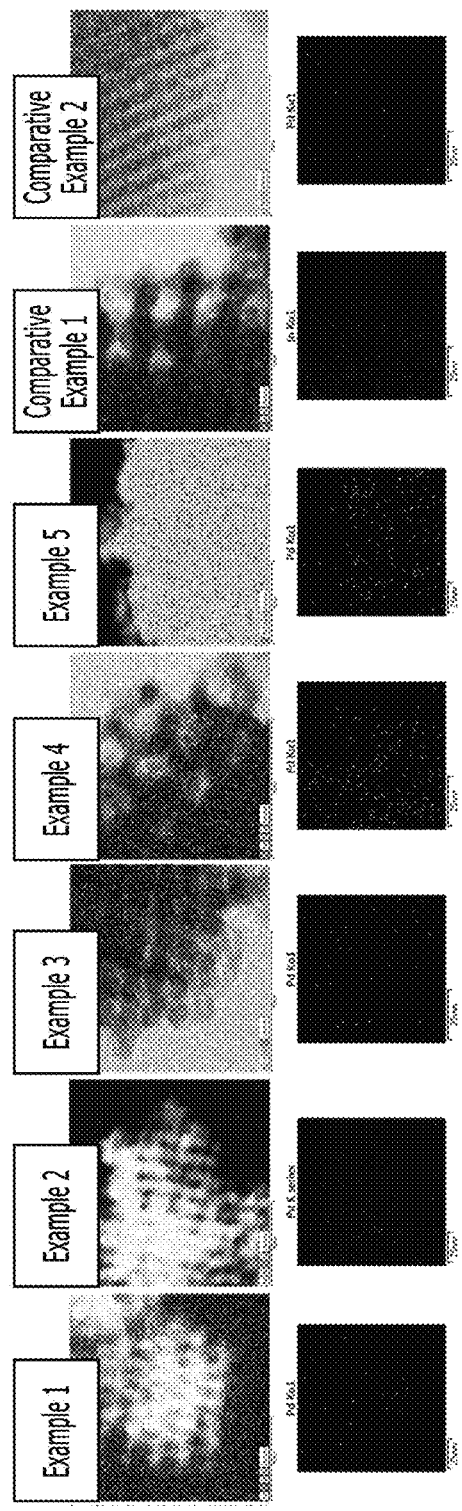
FIG. 6 shows a photograph showing results of energy dispersive X-ray spectroscopy (EDS) and X-ray fluorescence (XRF) analysis of an exemplary catalyst in Experimental Example 5.

As shown in FIG. 6 and Table 3, it can be seen that a degree of dispersion was evenly shown in EDS, and XRF indicates that an actual content of palladium increases as a theoretical content of palladium increases.

Experimental Example 6: N$_2$ Sorption Analysis

N$_2$ sorption analysis was performed to check a specific surface area, a pore diameter, and a porous structure of the prepared catalysts of Pd/m-In$_2$O$_3$, CeO$_2$/m-In$_2$O$_3$, and Ga$_2$O$_3$/m-In$_2$O$_3$.

Figure 7:
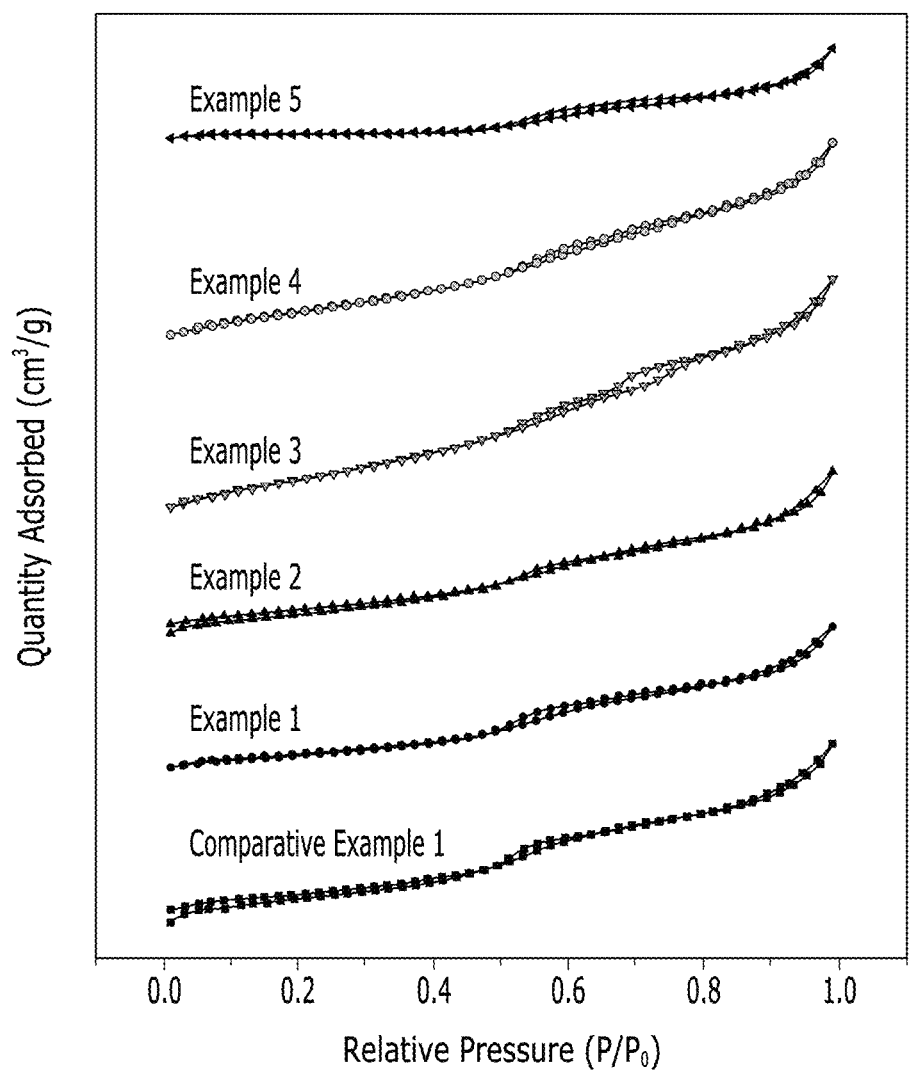
FIG. 7 and FIG. 8 shows a graph showing an analysis result of nitrogen adsorption and desorption ($N_2$ sorption) of an exemplary catalyst in Experimental Example 6.
Figure 8:
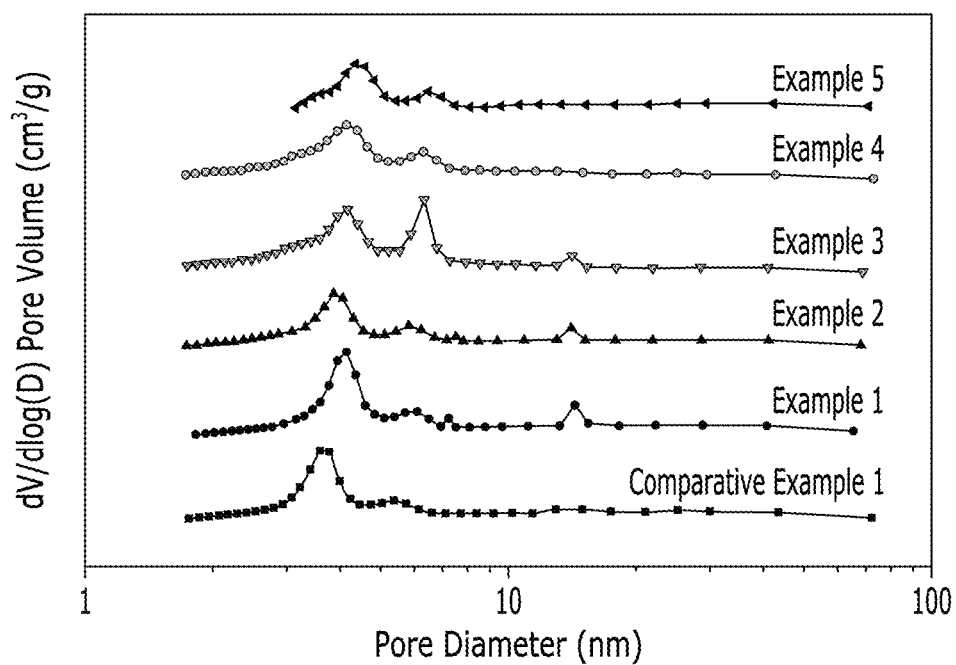

Specifically, the N$_2$ sorption analysis was performed to check specific surface area, pore diameter, and a porous structure of the prepared catalysts (Examples 1 to 5 and Comparative Example 1), and results thereof are shown in FIG. 7, FIG. 8, and Table 4.

TABLE 4

| Division | Catalyst | BET specific surface area (m$^2$/g) | Pore volume (cm$^3$/g) | Pore diameter (nm) |
|---|---|---|---|---|
| Example 1 | Pd(1)/m-In$_2$O$_3$ | 44.0 | 0.082 | 7.5 |
| Example 2 | Pd(3)/m-In$_2$O$_3$ | 47.8 | 0.088 | 7.3 |
| Example 3 | Pd(5)/m-In$_2$O$_3$ | 76.4 | 0.129 | 6.8 |
| Example 4 | Pd(7)/m-In$_2$O$_3$ | 60.6 | 0.107 | 7.1 |
| Example 5 | Pd(9)/m-In$_2$O$_3$ | 27.0 | 0.056 | 8.3 |
| Comparative Example 1 | m-In$_2$O$_3$ | 46.9 | 0.094 | 8.0 |

As shown in FIG. 7, FIG. 8, and Table 4, all supported catalysts showed a porous open form in a relative pressure-adsorption graph, and addition of a secondary catalyst affected a porous structure, but a basic frame was maintained in a pore diameter-pore volume graph.

In addition, a BET specific surface area in which the secondary catalyst was supported was close to or increased from m-In$_2$O$_3$, and a size of the mesopores was maintained without a significantly pore diameter change. The support of the secondary catalyst did not negatively affect the specific surface area or the pore size of the catalyst.

Experimental Example 7: Temperature Programmed Reduction (TPR) Analysis

Temperature programmed reduction (TPR) analysis was performed to determine a reduction degree of the prepared catalysts of Pd/m-In$_2$O$_3$, CeO$_2$/m-In$_2$O$_3$, and Ga$_2$O$_3$/m-In$_2$O$_3$. It was interpreted based on a pretreatment reduction temperature of 300° C. for actual hydrogenation of the carbon dioxide, and was performed by increasing a temperature thereof to a temperature of 900° C. to check a main peak of m-In$_2$O$_3$, and results thereof are shown in FIG. 9.

Figure 9:
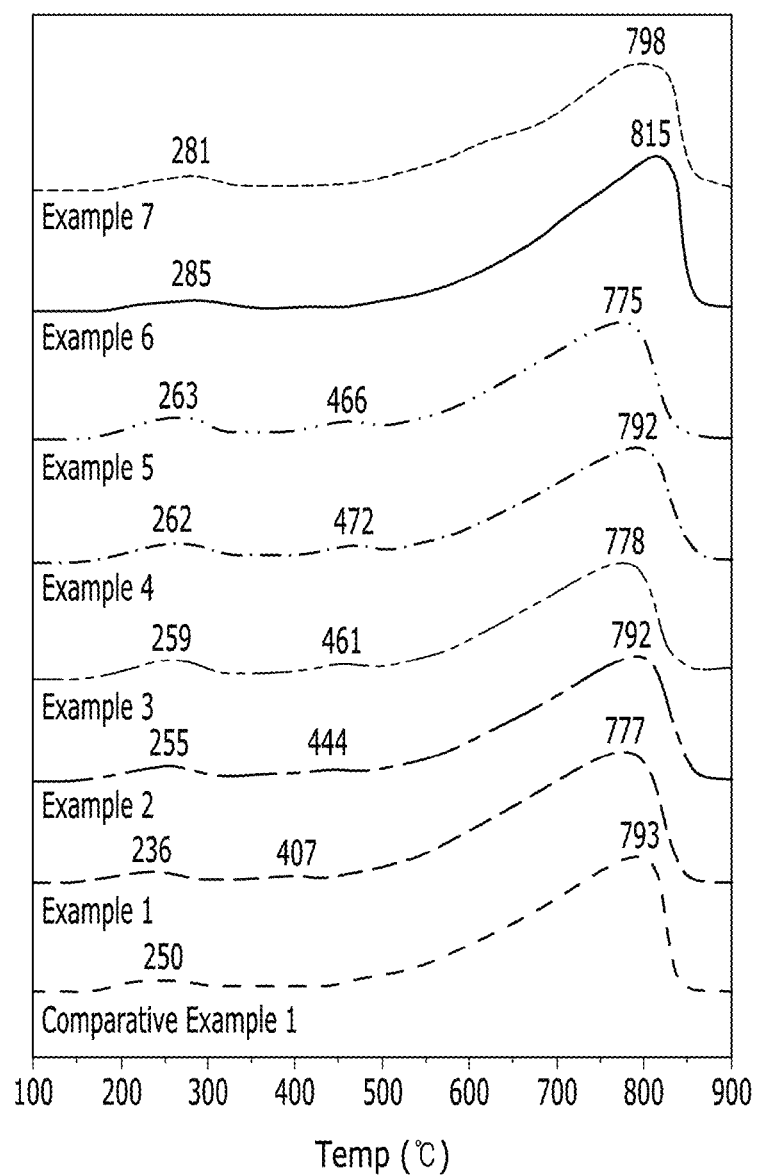
FIG. 9 shows a graph showing a result of temperature-raising reduction (TPR) analysis of an exemplary catalyst in Experimental Example 7.

As shown in FIG. 9, in the case of the palladium supported catalyst, as a content of the secondary catalyst increases, a reduction temperature of 300° C. or less was pushed backward, but all were below 300° C., which is a reduction condition of the actual reaction. In the case of cerium oxide and gallium oxide supported catalysts, the reduction was slower compared with m-In$_2$O$_3$, which is below 300° C. The reduction amount of the catalyst may be recognized by comparing areas, and all catalysts supporting secondary catalysts are reduced well below 300° C.

Experimental Example 8: Scanning Electron Microscope (SEM) Analysis

Figure 10:
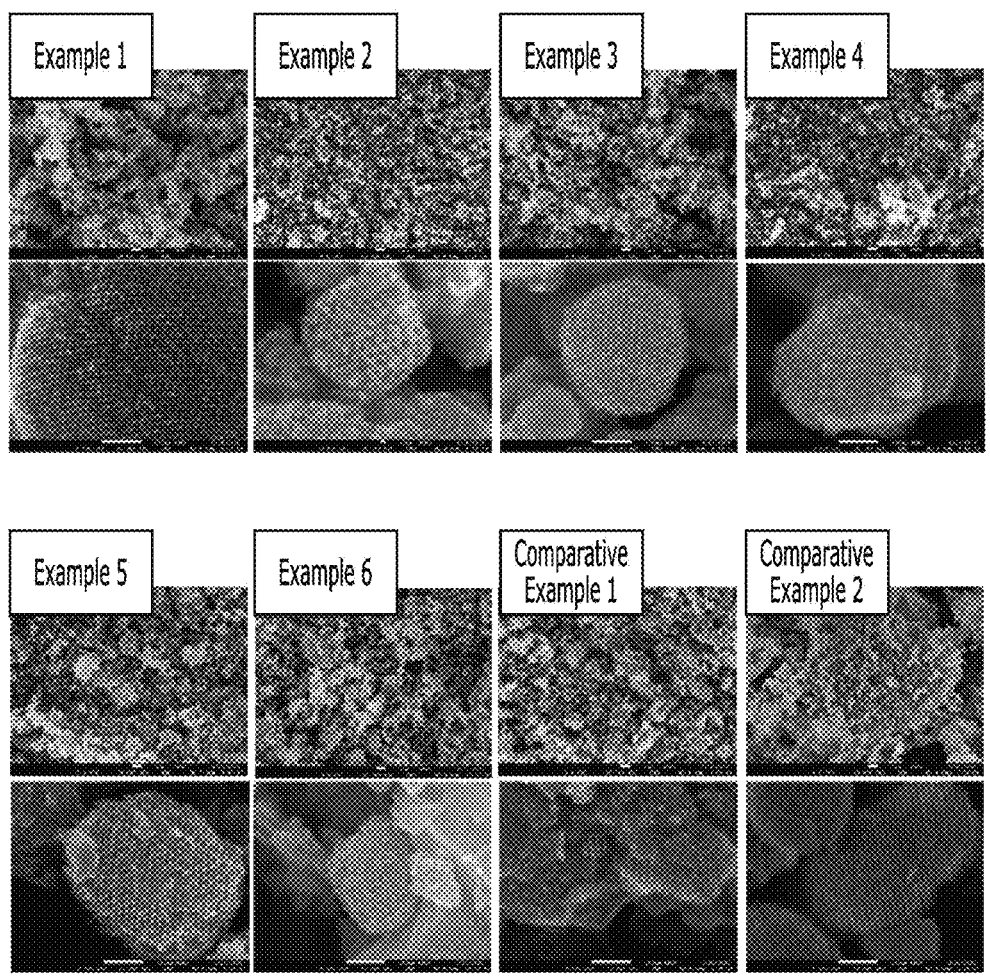
FIG. 10 illustrates a photograph showing a result of a scanning electron microscope (SEM) analysis of an exemplary catalyst in Experimental Example 8.

Images of the prepared catalysts of Pd/m-In$_2$O$_3$, CeO$_2$/m-In$_2$O$_3$, and Ga$_2$O$_3$/m-In$_2$O$_3$ were acquired through SEM analysis, and results thereof are shown in FIG. 10.

As shown in FIG. 10, all of the prepared catalysts uniformly exhibited a mesoporous structure, and the secondary catalyst was partially supported. Although not all of the secondary catalysts went into the pores, some were supported in the pores, and the porous structures were not damaged.

Experimental Example 9: Comparison of Catalyst Performance

Table 5 summarizes the performance of the prepared catalysts and catalysts disclosed in the related art.

TABLE 5

| Catalyst | Temperature (° C.) | Pressure (MPa) | CO$_2$ Conversion (%) | CH$_3$OH Selectivity (%) | CH$_3$OH Forming speed (mol/kg$_{cat}$ · h) | Ref |
|---|---|---|---|---|---|---|
| Cu/ZnO/ZrO$_2$ | 230 | 3 | 19.3 | 48.6 | 2.5 | 1 |
| Cu/ZnO/Al$_2$O$_3$ | 230 | 3 | 18.7 | 43.0 | 2.2 | |
| Cu/ZnO/ZrO$_2$/Al$_2$O$_3$ | 230 | 3 | 23.2 | 60.3 | 3.8 | |
| Cu/Ga$_2$O$_3$/ZrO$_2$ | 250 | 2 | 13.7 | 75.6 | 1.9 | 2 |
| Cu/B$_2$O$_3$/ZrO$_2$ | 250 | 2 | 15.8 | 67.3 | 1.8 | |
| Cu—Zn/SiO$_2$ | 270 | 2 | 1.8 | 99.1 | 3.6 | 3, 4 |
| PdMgAl | 250 | 3 | 0.3 | 4.0 | 0.0 | 5 |
| PdZnAl | 250 | 3 | 0.6 | 60.0 | 0.5 | |
| PdMgGa | 250 | 3 | 1 | 47.0 | 0.6 | |
| Pd(0.34)—Cu | 250 | 4.1 | 6.6 | 34.0 | 1.1 | 6 |
| In$_2$O$_3$ | 270 | 4 | 1.1 | 54.9 | 0.8 | 7 |
| In$_2$O$_3$ | 330 | 4 | 7.1 | 39.7 | 3.7 | |
| Example 1 Pd(1)/m-In$_2$O$_3$ | 280 | 5 | 9.6 | 46.2 | 3.9 | The present invention |
| Example 2 Pd(3)/m-In$_2$O$_3$ | 280 | 5 | 13.3 | 43.9 | 5.6 | |
| Example 3 Pd(5)/m-In$_2$O$_3$ | 280 | 5 | 14.7 | 44.0 | 5.4 | |
| Example 4 Pd(7)/m-In$_2$O$_3$ | 280 | 5 | 16.0 | 44.2 | 5.9 | |
| Example 5 Pd(9)/m-In$_2$O$_3$ | 280 | 5 | 15.6 | 44.3 | 5.4 | |
| Example 6CeO$_2$(3)/m-In$_2$O$_3$ | 320 | 5 | 7.1 | 29.4 | 1.8 | |
| Example 7 Ga$_2$O$_3$(3)/m-In$_2$O$_3$ | 320 | 5 | 10.2 | 19.4 | 1.7 | |
| Comparative Example 1 m-In$_2$O$_3$ | 280 | 5 | 3.0 | 36.1 | 0.9 | |
| Comparative Example 2 Pd(7)/SiO$_2$ | 280 | 5 | 1.5 | 2.9 | 0.0 | |

As shown in Table 5, Pd(1 to 9)/m-In$_2$O$_3$, CeO$_2$(3)/m-In$_2$O$_3$, and Ga$_2$O$_3$ (3)/m-In$_2$O$_3$ prepared in the above examples (Examples 1 to 7) generally had high conversion efficiency and methanol selectivity, and a relatively superior methanol production rate compared with catalysts reported in other research papers. When Pd was used as a secondary catalyst, it showed better performance compared with CeO$_2$ and Ga$_2$O$_3$, and the Pd supported at 7 wt % showed a highest methanol production rate, and thus an optimum content.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of greater than or equal to appended claims.

What is claimed is:

1. A catalyst for converting carbon dioxide to methanol, the catalyst comprising:
   mesoporous indium oxide; and
   a secondary catalyst supported on the mesoporous indium oxide,
   wherein a porous structure of the mesoporous indium oxide comprises Ia3d symmetry, and comprises mesopores and micropores interconnecting the mesopores,
   wherein the mesoporous indium oxide has a specific surface area of greater than about 40 m$^2$/g,
   a pore volume thereof is greater than about 0.05 cm3/g,
   wherein the secondary catalyst is formed of cerium oxide (CeO$_2$), gallium oxide (Ga$_2$O$_3$), or a combination thereof, and
   wherein the catalyst comprises an amount of about 1 wt % to 5 wt % of the cerium oxide or the gallium oxide secondary catalyst with respect to the total weight of the catalyst.

2. The catalyst of claim 1, wherein the mesoporous indium oxide has a particle size of about 15 nm to 20 nm and a size of the mesopores ranges from about 2 nm to 20 nm.

3. The catalyst of claim 1, wherein the mesoporous indium oxide is prepared using a mesoporous silica template.

4. A method of preparing a catalyst for conversion of carbon dioxide to methanol by hydrogenation, comprising:
   supporting a precursor of an indium oxide on a mesoporous silica template;

preparing mesoporous indium oxide by separating the mesoporous silica template from the precursor of the indium oxide; and supporting a secondary catalyst on the mesoporous indium oxide, wherein the catalyst comprises the mesoporous indium oxide, and the secondary catalyst supported on the mesoporous indium oxide, wherein a porous structure of the mesoporous indium oxide comprises Ia3d symmetry, and comprises mesopores and micropores interconnecting the mesopores, wherein the mesoporous indium oxide has a specific surface area of greater than about 40 m2/g, and a pore volume thereof is greater than about 0.05 cm$^3$/g, wherein the secondary catalyst is formed of cerium oxide ($CeO_2$), gallium oxide ($Ga_2O_3$), or a combination thereof, and wherein the catalyst comprises an amount of about 1 wt % to 5 wt % of the cerium oxide or the gallium oxide secondary catalyst with respect to the total weight of the catalyst.

5. The method of claim 4, wherein the supporting of the precursor of the indium oxide is performed by preparing a first solution comprising the precursor of the indium oxide and contacting the first solution with the mesoporous silica template.

6. The method of claim 5, wherein the first solution comprises an amount of about 5 wt % to 10 wt % of the indium oxide precursor with respect to the total weight of the first solution.

7. The preparing method of claim 5, wherein the supporting of the precursor of the indium oxide is performed by first drying the first solution and the mesoporous silica template on which the precursor of the indium oxide is supported at a temperature of about 20° C. to 30° C., second drying at a temperature of about 60° C. to 90° C., and firing at a temperature of about 300° C. to 550° C.

8. The method of claim 5, wherein the first solution comprises the precursor of the indium oxide in an amount of about 3 parts by weight to 5 parts by weight with respect to 1 part by weight of the mesoporous silica template.

9. The method of claim 4, wherein the preparing of the mesoporous indium oxide is performed by adding the mesoporous silica template on which the precursor of the indium oxide is supported into an alkaline aqueous solution, and reacting them at a temperature of about 70° C. to 90° C. for about 2 to 4 h.

10. The method of claim 4, wherein the supporting of the secondary catalyst is performed by preparing a second solution comprising a secondary precursor of the secondary catalyst and contacting the second solution with the mesoporous indium oxide.

11. The method of claim 10, wherein the second solution comprises an amount of about 1 wt % to 9 wt % of the secondary precursor with respect to the total weight of the second solution.

12. The method of claim 10, wherein the supporting of the secondary catalyst is performed by drying the second solution and the mesoporous indium oxide on which the precursor of the secondary catalyst is supported at a temperature of about 60° C. to 90° C. and firing it at a temperature of about 300° C. to 550° C.

* * * * *